(12) United States Patent
Sharkey et al.

(10) Patent No.: US 11,614,443 B2
(45) Date of Patent: *Mar. 28, 2023

(54) MULTIPLEX POLYMERIC DYE DEVICES AND METHODS FOR USING THE SAME

(71) Applicant: Becton, Dickinson and Company, Franklin Lakes, NJ (US)

(72) Inventors: Marybeth Sharkey, San Jose, CA (US); Shumeye Mamo, San Ramon, CA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 187 days.

This patent is subject to a terminal disclaimer.

(21) Appl. No.: 16/701,032

(22) Filed: Dec. 2, 2019

(65) Prior Publication Data

US 2020/0103398 A1 Apr. 2, 2020

Related U.S. Application Data

(63) Continuation of application No. 15/490,697, filed on Apr. 18, 2017, now Pat. No. 10,545,137.

(60) Provisional application No. 62/326,640, filed on Apr. 22, 2016.

(51) Int. Cl.
*G01N 33/52* (2006.01)
*G01N 33/58* (2006.01)

(52) U.S. Cl.
CPC ......... *G01N 33/525* (2013.01); *G01N 33/528* (2013.01); *G01N 33/582* (2013.01); *G01N 33/585* (2013.01)

(58) Field of Classification Search
CPC .. G01N 33/525; G01N 33/528; G01N 33/585; G01N 33/582
See application file for complete search history.

(56) References Cited

U.S. PATENT DOCUMENTS

| | | |
|---|---|---|
| 3,992,811 A | 11/1976 | Yellin |
| 3,999,948 A | 12/1976 | Diendoerfer et al. |
| 4,142,033 A | 2/1979 | Witenhafer |
| 4,193,980 A | 3/1980 | Clason et al. |
| 4,222,379 A | 9/1980 | Smith |
| 4,916,078 A | 4/1990 | Klose et al. |
| 4,919,890 A | 4/1990 | Arai et al. |
| 5,213,505 A | 5/1993 | Laipply |
| 5,225,285 A | 7/1993 | Hall |
| 5,593,587 A | 1/1997 | Fumihiko et al. |
| 5,945,341 A | 8/1999 | Howard |
| 6,221,655 B1 | 4/2001 | Fung et al. |
| 6,350,619 B1 | 2/2002 | Mercolino et al. |
| 7,141,436 B2 | 11/2006 | Gatto-Menking et al. |
| 7,144,950 B2 | 12/2006 | Bazan et al. |
| 7,211,443 B2 | 5/2007 | Woudenberg et al. |
| 7,214,489 B2 | 5/2007 | Bazan et al. |
| 7,270,956 B2 | 9/2007 | Bazan et al. |
| 7,332,329 B2 | 2/2008 | Wark et al. |
| 7,629,448 B2 | 12/2009 | Bazan et al. |
| 7,666,594 B2 | 2/2010 | Bazan et al. |
| 7,695,953 B2 | 4/2010 | Gould et al. |
| 7,807,448 B2 | 10/2010 | Glezer et al. |
| 7,811,755 B2 | 10/2010 | Bazan et al. |
| 7,842,475 B2 | 11/2010 | Zheng et al. |
| 7,867,751 B2 | 1/2011 | Jia et al. |
| 7,897,684 B2 | 3/2011 | Bazan et al. |
| 7,914,984 B2 | 3/2011 | Bazan et al. |
| 7,972,838 B2 | 7/2011 | Korpimaki et al. |
| 8,101,416 B2 | 1/2012 | Bazan et al. |
| 8,110,673 B2 | 2/2012 | Bazan et al. |
| 8,158,444 B2 | 4/2012 | Gaylord et al. |
| 8,216,530 B2 | 7/2012 | Handique et al. |
| 8,227,187 B2 | 7/2012 | Bazan et al. |
| 8,298,834 B2 | 10/2012 | Glezer et al. |
| 8,338,532 B2 | 12/2012 | Bazan et al. |
| 8,354,239 B2 | 1/2013 | Gaylord et al. |
| 8,362,193 B2 | 1/2013 | Gaylord et al. |
| 8,394,626 B2 | 3/2013 | Ramsey et al. |
| 8,455,613 B2 | 6/2013 | Gaylord et al. |
| 8,546,081 B2 | 10/2013 | Bazan et al. |
| 8,575,303 B2 | 11/2013 | Gaylord et al. |
| 8,609,044 B2 | 12/2013 | Ullin et al. |
| 8,617,814 B2 | 12/2013 | Bazan et al. |
| 8,669,055 B2 | 3/2014 | Bazan et al. |
| 8,759,444 B2 | 6/2014 | Bazan et al. |
| 8,802,450 B2 | 8/2014 | Gaylord et al. |

(Continued)

FOREIGN PATENT DOCUMENTS

| | | |
|---|---|---|
| CN | 102841195 A | 12/2012 |
| CN | 104704363 A | 6/2015 |

(Continued)

OTHER PUBLICATIONS

Hedley et al. "Novel Lymphocyte Screening Tube Using Dried Monoclonal Antibody Reagents," Cytometry Part B: Clinical Cytometry, 2015, vol. 88, No. 6, pp. 361-370.
Thakar et al. "CD4 estimating reagents in dry format are compatible with conventional flow cytometer; FACSCalibur for estimation of absolute CD4 count & percentages," The Indian Journal of Medical Research, vol. 137, No. 2, Feb. 2013, pp. 346-355.
"ReaPan 34845", Jan. 30, 2013 (Jan. 30, 2013). pp. 1-2. Retrieved from the Internet: URL:http://www.demo.reametrix.comjdownload/QMS/Product Inserts/ReaPan34845.pdf.
Communication The extended European search report for European Patent Application No. 17786484.0, dated Oct. 24, 2019, 6 pages.
Becton, Dickinson and Company, "BD Horizon Brilliant Dyes", 2021, Internet, URL: https://www.bdbiosciences.com/en-us/applications/research-applications/multicolor-flow-cytometry/brilliant-violet-dyes.

(Continued)

*Primary Examiner* — James W Rogers
(74) *Attorney, Agent, or Firm* — Bret E. Field; Bozicevic, Field & Francis LLP

(57) ABSTRACT

Multiplex polymeric dye devices are provided. Aspects of the devices include a solid support, and first and second dried polymeric dye compositions distinctly positioned relative to a surface of the solid support. Aspects of the invention further include methods of making and using the devices, e.g., in analyte detection applications, as well as kits containing the devices.

13 Claims, 4 Drawing Sheets

(56) References Cited

U.S. PATENT DOCUMENTS

| | | |
|---|---|---|
| 8,835,113 B2 | 9/2014 | Bazan et al. |
| 8,841,072 B2 | 9/2014 | Bazan et al. |
| 8,969,509 B2 | 3/2015 | Liu et al. |
| 8,980,572 B2 | 3/2015 | Wong et al. |
| 8,993,335 B2 | 3/2015 | Bazan et al. |
| 9,040,236 B2 | 5/2015 | Hill et al. |
| 9,085,799 B2 | 7/2015 | Bazan et al. |
| 9,096,894 B2 | 8/2015 | Iguchi et al. |
| 9,139,869 B2 | 9/2015 | Gaylord et al. |
| 9,159,465 B2 | 10/2015 | Bazan et al. |
| 9,371,559 B2 | 6/2016 | Bazan et al. |
| 9,383,353 B2 | 7/2016 | Gaylord et al. |
| 9,442,106 B2 | 9/2016 | Beck et al. |
| 9,547,008 B2 | 1/2017 | Gaylord et al. |
| 9,857,365 B2 | 1/2018 | Choi et al. |
| 9,878,323 B2 | 1/2018 | Glezer et al. |
| 10,161,935 B2 | 12/2018 | Fujiwara et al. |
| 2001/0036423 A1 | 11/2001 | Kawasaki et al. |
| 2003/0006141 A1 | 1/2003 | Gerlach et al. |
| 2003/0012714 A1 | 1/2003 | Taylor et al. |
| 2003/0108973 A1 | 6/2003 | Gatto-Menking et al. |
| 2003/0143755 A1 | 7/2003 | Davis et al. |
| 2003/0207465 A1 | 11/2003 | Davis et al. |
| 2003/0219908 A1 | 11/2003 | Davis et al. |
| 2004/0092036 A1 | 5/2004 | Chen et al. |
| 2006/0040408 A1 | 2/2006 | Jones et al. |
| 2006/0182655 A1 | 8/2006 | Zou |
| 2007/0054341 A1 | 3/2007 | Gatto-Menking et al. |
| 2007/0202538 A1 | 8/2007 | Glezer et al. |
| 2007/0243601 A1 | 10/2007 | Korpimaki et al. |
| 2008/0194508 A1 | 8/2008 | Christensen et al. |
| 2008/0241962 A1 | 10/2008 | Wang |
| 2008/0274512 A1 | 11/2008 | Squirrell et al. |
| 2009/0011518 A1 | 1/2009 | Lindberg |
| 2009/0176213 A1 | 7/2009 | Zheng et al. |
| 2010/0015628 A1 | 1/2010 | Farchaus et al. |
| 2010/0330684 A1 | 2/2010 | O'Connor |
| 2010/0172801 A1 | 7/2010 | Pugia et al. |
| 2010/0184059 A1 | 7/2010 | Lee et al. |
| 2010/0285520 A1 | 11/2010 | Halverson et al. |
| 2011/0015091 A1 | 1/2011 | Glezer et al. |
| 2011/0257374 A1 | 10/2011 | Gaylord et al. |
| 2011/0291076 A1 | 12/2011 | Shukla et al. |
| 2012/0070385 A1 | 3/2012 | Liu |
| 2012/0183961 A1 | 7/2012 | Han et al. |
| 2012/0301943 A1 | 11/2012 | Iguchi et al. |
| 2013/0052650 A1 | 2/2013 | Kavanagh |
| 2013/0065788 A1 | 3/2013 | Glezer et al. |
| 2013/0089853 A1 | 4/2013 | Li |
| 2014/0271481 A1 | 9/2014 | Boday et al. |
| 2014/0302516 A1 | 10/2014 | Chiu |
| 2014/0319379 A1 | 10/2014 | Manian |
| 2015/0125882 A1 | 5/2015 | Bornheimer et al. |
| 2015/0174547 A1 | 6/2015 | Emans et al. |
| 2015/0226746 A1 | 8/2015 | Bazan et al. |
| 2016/0266132 A1 | 9/2016 | Gaylord et al. |
| 2016/0299164 A1 | 10/2016 | Ackerman et al. |
| 2016/0320415 A1 | 11/2016 | Manneh |
| 2016/0341720 A1 | 11/2016 | Bazan et al. |
| 2016/0349267 A1 | 12/2016 | Gaylord et al. |
| 2017/0010199 A1 | 1/2017 | Halverson et al. |
| 2017/0023563 A1 | 1/2017 | Hirano et al. |
| 2017/0115298 A1 | 4/2017 | Gaylord et al. |
| 2017/0189902 A1 | 7/2017 | Moran |
| 2017/0307600 A1 | 10/2017 | Sharkey et al. |
| 2018/0031554 A1 | 2/2018 | Beck et al. |
| 2018/0078241 A1 | 3/2018 | Moga et al. |
| 2018/0143108 A1 | 5/2018 | Madsen et al. |
| 2018/0154353 A1 | 6/2018 | Glezer et al. |
| 2018/0224460 A1 | 8/2018 | Inokuma et al. |
| 2019/0004075 A1 | 1/2019 | Ackerman et al. |
| 2020/0147615 A1 | 5/2020 | Huang |

FOREIGN PATENT DOCUMENTS

| | | |
|---|---|---|
| CN | 105358977 A | 2/2016 |
| EP | 0225703 | 6/1987 |
| EP | 0464942 | 1/1992 |
| JP | H0374405 | 3/1991 |
| JP | H0374405 A | 3/1991 |
| JP | 2013007751 A | 1/2013 |
| JP | 2013517374 A | 5/2013 |
| JP | 2013165709 A | 8/2013 |
| JP | 2014001949 A | 1/2014 |
| JP | 2015102337 A | 6/2015 |
| JP | 2015528114 A | 9/2015 |
| KR | 101495631 | 2/2015 |
| WO | WO 2004/001379 A2 | 12/2003 |
| WO | WO 2004/077014 A2 | 9/2004 |
| WO | WO 2004/092324 A2 | 10/2004 |
| WO | WO 2005/086617 A2 | 9/2005 |
| WO | WO2005118863 A2 | 12/2005 |
| WO | WO2006003423 | 1/2006 |
| WO | WO 2006/074471 A2 | 7/2006 |
| WO | WO 2006/074482 A2 | 7/2006 |
| WO | WO 2006/083932 A2 | 8/2006 |
| WO | WO 2008/100344 A2 | 8/2008 |
| WO | WO 2010/151807 A1 | 12/2010 |
| WO | WO 2011/091086 A1 | 7/2011 |
| WO | WO2011105507 A | 6/2013 |
| WO | WO2015175861 A | 11/2015 |
| WO | WO2017123622 A1 | 7/2017 |
| WO | WO2017/222998 | 12/2017 |

OTHER PUBLICATIONS

Bergeron, et al., "Evaluation of a Dry Format Reagent Alternative for CD4 T-Cell Enumeration for the FACSCount System: A Report on a Moroccan-Canadian Study", Cytometry, 2010, vol. 78B, p. 188-193.

MULTIPLEX POLYMERIC DYE DEVICES AND METHODS FOR USING THE SAME

CROSS-REFERENCE TO RELATED APPLICATIONS

Pursuant to 35 U.S.C. § 119(e), this application claims priority to the filing date of U.S. Provisional Patent Application Ser. No. 62/326,640, filed Apr. 22, 2016; the disclosure of which application is incorporated herein by reference.

INTRODUCTION

Assays for determining the presence and concentration of analytes in a biological sample fluid often rely on the specific binding of a detectable label to the target analyte. The detectable label may be a marker that can be visualized either by an unaided eye or detectable by spectroscopy, such as fluorescence or UV-vis spectroscopy. Typically, fluorescent dyes may be used as the detectable label, where the fluorescent dye includes a particular fluorochrome. A fluorochrome may have a certain properties, such as its absorption spectrum, its extinction coefficient at a wavelength convenient for excitation, its emission spectrum, and its quantum efficiency. Quantum efficiency is the number of photons emitted for every photon absorbed.

The properties of a fluorochrome may depend on its surrounding environment. For example, some fluorochromes, such as fluorescein, are sensitive to pH. Fluorescence can also be quenched by an interaction with another molecule in which the emission energy of the dye is dissipated by a non-radiative transition. In some cases, the detectable fluorescence of a fluorochrome can be quenched by interactions between the molecules of another fluorochrome, such as a fluorochrome of another dye. This effect can be observed as an undesirable dye-dye interaction where the fluorescence of a dye is significantly less than would be expected as compared to the dye's fluorescence in the absence of other interfering dyes.

SUMMARY

Multiplex polymeric dye devices are provided. Aspects of the devices include a reagent device having a solid support, and first and second dried polymeric dye compositions distinctly positioned relative to a surface of the solid support. Aspects of the invention further include methods of making and using the devices, e.g., in analyte detection applications, as well as kits containing the devices.

DETAILED DESCRIPTION

Figure 1:
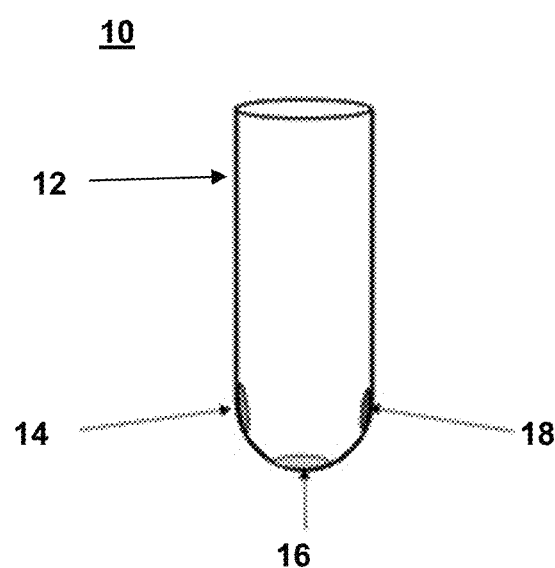
FIG. 1 is an illustration of a reagent device that includes three distinctly positioned dried polymeric dye compositions, according to embodiments of the present disclosure.

Multiplex polymeric dye devices are provided. Aspects of the devices include a solid support, and first and second dried polymeric dye compositions distinctly positioned relative to a surface of the solid support. Aspects of the invention further include methods of making and using the devices, e.g., in analyte detection applications, as well as kits containing the devices.

Before embodiments of the present disclosure are described in greater detail, it is to be understood that these embodiments are not limited to the particular embodiments described, as such may vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the embodiments of the present disclosure. The upper and lower limits of these smaller ranges may independently be included in the smaller ranges and are also encompassed within the embodiments of the present disclosure, subject to any specifically excluded limit in the stated range. Where the stated range includes one or both of the limits, ranges excluding either or both of those included limits are also included in the embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the embodiments of the present disclosure. Any recited method can be carried out in the order of events recited or in any other order which is logically possible.

As summarized above, the present disclosure provides reagent devices that include a solid support and first and second dried polymeric dye compositions distinctly positioned relative to a surface of the solid support. In further describing various embodiments of the invention, the subject reagent devices are first described in greater detail. Next, methods of using the subject reagent devices are described. In addition, methods of making the subject reagent devices, as well as kits that include the subject reagent devices, are also provided.

Reagent Devices

Aspects of the present disclosure include reagent devices. In certain embodiments, the reagent devices are useful in assays, for example assays of a liquid sample, such as a biological sample, e.g., for the presence of one or more analytes in the sample. Reagent devices according to certain embodiments of the present disclosure include a solid support and first and second dried polymeric dye compositions distinctly positioned relative to a surface of the solid support.

The solid support included in embodiments of the reagent device can be any convenient solid support that is compatible with the liquid sample and/or reagent(s) or analyte(s) in contact with the reagent device. For example, the solid support can be a liquid-compatible solid support for reagent devices configured to contain a liquid sample. In some cases, the liquid sample may be an aqueous liquid sample, and in these cases, the solid support may be compatible with aqueous samples. By "compatible" is meant that the solid support is substantially inert (e.g., does not significantly react with) the liquid and/or reagent(s) or analyte(s) in contact with the solid support.

The solid support may be configured as a container, where the container is configured to hold a certain volume of a fluid (e.g., gas or liquid). In certain embodiments, the solid support is configured as a liquid container. For example, the liquid container may be configured to hold a volume of a liquid. The size of the liquid container may depend on the volume of liquid to be held in the liquid container. For instance, the liquid container may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the liquid container is configured to hold a volume (e.g., a volume of a liquid) ranging from 0.1 ml to 200 ml.

The shape of the solid support may also vary and may depend on the use of the reagent device. For example, as described herein, the reagent device may find use in an assay, such as an assay of a liquid sample (e.g., a biological sample). In these cases, the solid support may be configured in a shape that is compatible with the assay and/or the method or other devices used to perform the assay. For instance, the solid support may be configured in a shape of typical laboratory equipment used to perform the assay or in a shape that is compatible with other devices used to perform the assay. As described above, the solid support may be configured as a liquid container. In these embodiments, the liquid container may be a vial or a test tube. In certain cases, the liquid container is a vial. In certain cases, the liquid container is a test tube. As described above, the liquid container may be configured to hold a volume (e.g., a volume of a liquid). In embodiments where the liquid container is a vial or a test tube, the liquid container may be configured to hold a volume (e.g., a volume of a liquid) ranging from 0.1 ml to 1000 ml, such as from 0.5 ml to 900 ml, or 0.5 ml to 800 ml, or 0.5 ml to 700 ml, or 0.5 ml to 600 ml, or 0.5 ml to 500 ml, or 0.5 ml to 400 ml, or 0.5 ml to 300 ml, or 0.5 ml to 200 ml, or 0.5 ml to 100 ml, or 0.5 ml to 50 ml, or 0.5 ml to 25 ml, or 0.5 ml to 10 ml, or 0.5 ml to 5 ml, or 1 ml to 5 ml. In certain instances, the vial or test tube is configured to hold a volume (e.g., a volume of a liquid) ranging from 0.5 ml to 5 ml.

In other embodiments, the solid support is configured as a multi-well plate. In these cases, the solid support may include a plurality of liquid containers (e.g., wells), such as 2 or more, or 10 or more, or 50 or more, or 75 or more, or 100 or more, or 300 or more, or 500 or more, or 750 or more, or 1000 or more or 1500 or more, or 2000 or more liquid containers (e.g., wells). Examples of solid supports configured as multi-well plates may include, for example, 6, 24, 96, 384 or 1536 liquid containers (e.g., wells). In embodiments where the liquid container is a well of a multi-well plate, an individual well may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the vial or test tube is configured to hold a volume (e.g., a volume of a liquid) ranging from 0.1 ml to 25 ml.

As described above, embodiments of the solid support of the reagent device can be compatible with the liquid sample and/or reagent(s) or analyte(s) in contact with the reagent device. Examples of suitable solid support materials for the reagent devices include, but are not limited to, glass and plastic. For example, the solid support may be composed of glass, such as, but not limited to, silicate glass, borosilicate glass, sodium borosilicate glass (e.g., PYREX™) fused quartz glass, fused silica glass, and the like. Other examples of suitable solid support materials for the reagent devices include plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

In some embodiments, as described above, the solid support is configured as a container, where the container is configured to hold a certain volume of a fluid (e.g., gas or liquid). In some instances, a solid support is configured as a container (e.g., a liquid container). In some embodiments where the solid support is configured as a liquid container, the liquid container may be sealed. That is, the liquid container may include a seal that substantially prevents the contents of the liquid container (e.g., liquid inside the liquid container) from exiting the liquid container. The seal of the liquid container may also substantially prevent other substances from entering the liquid container. For example, the seal may be a water-tight seal that substantially prevents liquids from entering or exiting the container, or may be an air-tight seal that substantially prevents gases from entering or exiting the container. In some instances, the seal is a removable or breakable seal, such that the contents of the liquid container may be exposed to the surrounding environment when so desired, e.g., if it is desired to remove a portion of the contents of the liquid container. In some instances, the seal is made of a resilient material to provide a barrier (e.g., a water-tight and/or air-tight seal) for retaining a sample in the container. Particular types of seals include, but are not limited to, films, such as polymer films, caps, etc., depending on the type of container. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

As described above, the solid support may be configured as a container, where the container is configured to hold a certain volume of a fluid (e.g., gas or liquid). In some instances, a solid support that is configured as a container (e.g., a liquid container) has an inner surface and an outer surface. In these embodiments, the inner surface of the solid support (e.g., container) is the surface of the solid support (e.g., container) facing toward the inside of the solid support (e.g., container). The inner surface may be in contact with the contents of the container. As such, the solid support may include an inner surface of the container, such as an inner surface of a liquid container. The outer surface of the solid support (e.g., container) is the surface of the solid support (e.g., container) facing away from the inside of the solid support (e.g., container). The outer surface does not contact the contents of the container. As such, the solid support may include an outer surface of the container, such as an outer surface of a liquid container.

In certain embodiments, the reagent device includes a dye composition positioned on a surface of the solid support. The reagent device may include one or more dye compositions on the surface of the solid support, such as 2 or more dye compositions, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, 16 or more, or 17 or more, or 18 or more, or 19 or more, or 20 or more, or 25 or more, or 30 or more, or 35 or more, or 40 or more, or 45 or more, or 50 or more dye compositions on the surface of the solid support. In some embodiments, the reagent device includes 2 to 50 dye compositions on the surface of the solid support, such as 2 to 40, or 2 to 30 or 2 to 20 or 2 to 15, or 2 to 10, or 2 to 7, or 2 to 5 dye compositions on the surface of the solid support. For example, the reagent device may include 2, or 3, or 4, or 5, or 6, or 7, or 8, or 9, or 10, or 11, or 12, or 13, or 14, or 15, or 16, or 17, or 18, or 19, or 20 dye compositions on the surface of the solid support. In certain cases, the reagent device includes 2 dye compositions on the surface of the solid support. In certain cases, the reagent device includes 5 dye compositions on the surface of the solid support. In certain cases, the reagent device includes 7 dye compositions on the surface of the solid support. In certain cases, the reagent device includes 10 dye compositions on the surface of the solid support.

As described above, the reagent device may include two or more dye compositions positioned relative to a surface of the solid support. The dye compositions may be located on the surface of the solid support in distinct positions. For example, first and second dye compositions may be distinctly positioned on the surface of the solid support. By "distinct position" or "distinctly positioned" is meant that a dye composition is disposed at a position different from the position of another dye composition. The position of a dye composition may refer to the location of the dye composition on the surface of the solid support, and/or may refer to the position of the dye composition relative to the surface of the solid support. In some cases, a dye composition occupies a defined volume of space. For example, a dye composition may occupy a volume of space on a surface of the solid support. A distinctly positioned dye composition may occupy a volume of space that does not significantly coincide or overlap with a volume of space occupied by another dye composition, where in some instances it does not does not coincide or overlap at all with a volume of space occupied by another dye composition. Embodiments where dye compositions are distinctly positioned may provide for a minimization in dye-dye interactions between each of the dye compositions.

Stated another way, a distinctly positioned dye composition is not significantly mixed together with another polymeric dye composition, e.g., substantially no portion of the distinctly positioned dye composition is mixed with a portion of another polymeric dye composition. In some instances, a distinctly positioned dye composition is not mixed together with another polymeric dye composition, e.g., no portion of the distinctly positioned dye composition is mixed with a portion of another polymeric dye composition. In certain embodiments, a distinctly positioned dye composition includes a single dye. For example, a distinctly positioned dye composition may be substantially composed of a single dye and does not include another dye in a significant amount. A distinctly positioned dye composition may include a large excess of a dye with respect to any other dye that may be in the dye composition, such as, for example, 75 wt % or more, such as 80 wt % or more, or 85 wt % or more, or 90 wt % or more, or 95 wt % or more, or 97 wt % or more or 99 wt % or more, or 100 wt % of a dye with respect to any other dye that may be in the dye composition.

In some instances, distinctly positioned dye compositions are spaced apart from each other at separate locations on the surface of the solid support. A dye composition that is spaced apart from another dye composition may be physically separated from adjacent dye compositions. For instance, distinctly positioned dye compositions may be positioned on the surface of the solid support at separate locations such that there is a certain distance between an edge of the dye composition and an edge of an adjacent dye composition. In some embodiments, the distance between the separate locations of the dye compositions on the surface of the solid support is 0.1 mm or more, such as 0.5 mm or more, or 1 mm or more, or 2 mm or more, or 3 mm or more, or 4 mm or more, or 5 mm or more, or 6 mm or more, or 7 mm or more, or 8 mm or more, or 9 mm or more, or 10 mm or more, or 12 mm or more, or 14 mm or more, or 16 mm or more, or 18 mm or more, or 20 mm or more, or 25 mm or more or 30 mm or more, or 35 mm or more, or 40 mm or more, or 50 mm or more, or 60 mm or more, or 70 mm or more, or 80 mm or more, or 90 mm or more, or 100 mm or more, or 110 mm or more, or 120 mm or more, or 130 mm or more, or 140 mm or more, or 150 mm or more, or 160 mm or more, or 170 mm, or more, or 180 mm or more, or 190 mm or more, or 200 mm or more. For example, the distance between the separate locations of the dye compositions on the surface of the solid support may range from 0.1 mm to 200 mm, such as from 0.1 mm to 190 mm, or 0.1 mm to 180 mm, or 0.1 mm to 170 mm, or 0.1 mm to 160 mm, or 0.1 mm to 150 mm, or 0.1 mm to 140 mm, or 0.1 mm to 130 mm, or 0.1 mm to 120 mm, or 0.1 mm to 110 mm, or 0.1 mm to 100 mm, or 0.1 mm to 90 mm, or 0.1 mm to 80 mm, or 0.1 mm to 70 mm, or 0.1 mm to 60 mm, or 0.1 mm to 50 mm, or 0.1 mm to 40 mm, or 0.1 mm to 30 mm, or 0.1 mm to 20 mm, or 0.1 mm to 10 mm, or 0.1 mm to 9 mm, or 0.1 mm to 8 mm, or 0.1 mm to 7 mm, or 0.1 mm to 6 mm, or 0.1 mm to 5 mm, or 0.1 mm to 4 mm, or 0.1 mm to 3 mm, or 0.1 mm to 2 mm, or 0.1 mm to 1 mm, or 0.1 mm to 0.5 mm. In certain instances, the distance between the separate locations of the dye compositions on the surface of the solid support ranges from 0.1 mm to 200 mm. In some cases, the distance between the separate locations of the dye compositions on the surface of the solid support ranges from 0.1 mm to 10 mm.

In certain embodiments, distinctly positioned dye compositions are positioned adjacent to each other on the surface of the solid support, but are not spaced apart from each other. In these instances, an edge of a dye composition may contact the edge of an adjacent dye composition. For example, the volume of space occupied by a dye composition may contact, but not significantly overlap with a volume of space occupied by another (adjacent) dye composition. In these embodiments, adjacent dye compositions may contact each other, but are not significantly mixed together, e.g., substantially no portion of the distinctly positioned dye composition is mixed with a portion of another (adjacent) dye composition.

Distinctly positioned dye compositions may be present on the same surface of the solid support, but may be disposed at different positions on or relative to the surface of the solid support. For example, as described above, the solid support may be configured as a liquid container and, as such, may include an inner surface and an outer surface. In certain instances, the dye compositions are positioned on a surface (e.g., an inner surface) of the liquid container. In some cases, the dye compositions are distinctly positioned on an inner surface of the liquid container.

Examples of distinctly positioned dye compositions include embodiments where a dye composition is disposed on a surface of a solid support at a certain location and another dye composition is also disposed on the surface of the solid support at a different location. As such, the distinctly positioned dye compositions may be positioned at separate locations on the surface of the solid support. For example, embodiments of the reagent devices may include first and second dye compositions, where the first dye composition is positioned at a certain location on the surface of the solid support and the second dye composition is positioned on the surface of the solid support at a different location than the first dye composition. As described above, the first and second dye compositions may be spaced apart from each other such that there is a distance between the separate locations of the first and second dye compositions on the surface of the solid support. The distance between the first and second dye compositions may be according to the ranges and values as described above.

Additional dye compositions may be provided on the surface of the solid support. For example, the reagent device may include a third dye composition distinctly positioned on the surface of the solid support. The third dye composition may be distinctly positioned relative to the first dye composition, and also may be distinctly positioned relative to the second dye composition. As such, each of the dye compositions (e.g., first, second and third dye compositions) may be distinctly positioned relative to each other on the surface of the solid support, as described herein. Additional distinctly positioned dye compositions may be provided on the surface of the solid support, such as 4 or more distinctly positioned dye compositions, or 5 or more, 7 or more, 10 or more, etc., as described above.

Additional examples of distinctly positioned dye compositions include embodiments where a dye composition is disposed on a surface of a solid support at a certain location and another dye composition is located at the same location. As such, the distinctly positioned dye compositions may be co-located at the same location of the surface of the solid support. Dye compositions may be co-located at the same location yet still be distinctly positioned. For example, dye compositions may be separated from each other by a non-dye material. In some cases, the non-dye material is interposed between distinctly positioned dye compositions. The non-dye material may substantially cover a surface of a dye composition such that an adjacent dye composition is separated from the dye composition. For instance, a dye composition may have a non-dye material disposed over the surface of the dye composition, and another dye composition may be disposed on a surface of the non-dye material. In these instances, the dye composition may be physically separated from other dye compositions by the non-dye material. In some cases, the distinctly positioned dye compositions may be provided as alternating layers of a dye composition and a non-dye material on a surface of the solid support. As such, in certain embodiments, two or more dye compositions are distinctly positioned relative to each other and are also co-located at the same location of the surface of the solid support.

In certain embodiments, the non-dye material is a material compatible with other assay components (e.g., reagents, buffers, analytes, etc.) that may be present in the reagent device during use. The non-dye material may be substantially inert with respect to the other assay components (e.g., reagents, buffers, analytes, etc.) that may be present in the reagent device during use such that there is no significant reaction between the non-dye material and the other assay components. Examples of non-dye materials include, but are not limited to, stabilizers, buffers, soluble inert materials (e.g., aqueous soluble inert materials), and the like. Stabilizers of interest include, but are not limited to: sugars and polyalcohols. Sugars and polyalcohols suitable for use in lyophilized dye compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof. Non-dye materials may include, for example, bovine serum albumin (BSA), sodium azide, glycerol, phenylmethanesulfonyl fluoride (PMSF), ethylenediaminetetraacetic acid (EDTA), buffered citrate, phosphate buffered saline (PBS), sodium chloride, paraformaldehyde, and the like, and combinations thereof.

For example, embodiments of the reagent devices may include first and second dye compositions, where the first dye composition is positioned at a certain location on the surface of the solid support and the second dye composition is co-located at the same location as the first dye composition. As described above, the first and second dye compositions may be spaced apart from each other such that there is a distance between the first and second dye compositions. For instance, the first and second dye compositions may be separated from each other by a non-dye material, as described above. The distance between the first and second dye compositions may be according to the ranges and values as described above. For example, the non-dye material may be interposed between the distinctly positioned first and second dye compositions. In these embodiments, the first dye composition may be positioned on a surface of the solid support, the non-dye material may be disposed as a layer on a surface of the first dye composition, and the second dye composition may be disposed on the surface of the non-dye composition. In these instances, the first dye composition may be physically separated from the second dye compositions by the non-dye material. As such, in certain embodiments, the first and second dye compositions are distinctly positioned relative to each other and are also co-located at the same location of the surface of the solid support. For example, the layer of non-dye material on the surface of the first dye composition may substantially cover the entire surface of the first dye composition. In these instances, a second dye composition disposed on the surface of the non-dye composition may not significantly contact the first dye composition. In some cases, the non-dye material is a substantially contiguous layer of non-dye material on the surface of the first dye composition. For example, the non-dye material may cover a substantial portion of the surface of the first dye composition, such as 75% or more of the surface of the first dye composition, or 80% or more, or 85% or more, or 90% or more, or 95% or more, or 97% or more, or 99% or more of the surface of the first dye composition. Embodiments where the surface of the first dye composition is substantially covered by the non-dye material may provide for a minimization in dye-dye interactions between the first and second dye compositions.

In certain embodiments, the non-dye material has a thickness ranging from 0.01 mm to 5 mm, such as from 0.05 mm to 5 mm, or 0.1 mm to 5 mm, or 0.1 mm to 4 mm, or 0.1 mm to 3 mm, or 0.1 mm to 2 mm, or 0.1 mm to 1 mm, or 0.1 mm to 0.9 mm, or 0.1 mm to 0.8 mm, or 0.1 mm to 0.7 mm, or 0.1 mm to 0.6 mm, or 0.1 mm to 0.5 mm. In certain instances, the non-dye material has a thickness from 0.1 mm to 1 mm. In some cases, the non-dye material has a thickness from 0.1 mm to 0.05 mm.

Additional dye compositions may also be provided. For example, the reagent device may include a third dye composition distinctly positioned relative to the first and second dye compositions. As such, the third dye composition may be distinctly positioned relative to the first dye composition, and also may be distinctly positioned relative to the second dye composition. Thus, each of the dye compositions (e.g., first, second and third dye compositions) may be distinctly positioned relative to each other, as described herein. In some cases, each of the dye compositions may be separated from each other by a non-dye material. For instance, each of the dye compositions may be separated from each other by a non-dye material. In some cases, the non-dye material is interposed between each of the distinctly positioned dye compositions. In certain instances, each of the distinctly positioned dye compositions is provided as a layer with a layer of the non-dye material in between each of the distinctly positioned dye compositions. Additional layers of distinctly positioned dye compositions may be provided, such as 4 or more distinctly positioned dye compositions, or 5 or more, 7 or more, 10 or more, etc., as described above. As such, a plurality of dye compositions can be distinctly positioned relative to each other and also co-located at the same location of the surface of the solid support.

In certain embodiments, the dye compositions on the surface of the solid support are dried dye compositions. A dried dye composition is a dye composition that includes a low amount of solvent. For example, dried dye compositions may include a low amount of a liquid, such as water. In some cases, a dried dye composition includes substantially no solvent. For instance, dried dye compositions may include substantially no liquid, such as water. In certain embodiments, a dried dye composition includes 25 wt % or less solvent, such as 20 wt % or less, or 15 wt % or less, or 10 wt % or less, or 5 wt % or less, or 3 wt % or less, or 1 wt % or less, or 0.5 wt % or less solvent. In some cases, a dried dye composition is not a fluid. In some cases, a dried dye composition is substantially a solid. For example, a dried dye composition may have a high viscosity, such as a viscosity of 10,000 cP or more, or 25,000 cP or more, or 50,000 cP or more, or 75,000 cP or more, or 100,000 cP or more, or 150,000 cP or more, or 200,000 cP or more, or 250,000 cP or more at standard conditions.

In some instances, the dye compositions are lyophilized dye compositions. In certain cases, a lyophilized dye composition is a dye composition where water has been removed from the dye composition by sublimation, where the water in the dye composition undergoes a phase transition from a solid to a gas. For example, a lyophilized dye composition may be a dye composition where water has been removed from the composition by freezing the dye composition (e.g., freezing water in the dye composition) and then reducing the pressure surrounding the dye composition such that the water in the dye composition undergoes sublimation. In certain instances, a lyophilized dye composition includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In some cases, a lyophilized dye composition has 3% or less water as measured by Karl Fischer titration. In some cases, a lyophilized dye composition has 1% or less water as measured by Karl Fischer titration. In some cases, a lyophilized dye composition has 0.5% or less water as measured by Karl Fischer titration. Lyophilized dye compositions may include additives and/or excipients, such as a stabilizer. In some cases, the lyophilized dye composition includes a stabilizer, such as a sugar or a polyalcohol. Sugars and polyalcohols suitable for use in lyophilized dye compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof.

The dye in the dye composition may be used as a detectable label. In certain cases, the dye includes detectable moieties or markers that are detectible based on, for example, fluorescence emission maxima, fluorescence polarization, fluorescence lifetime, light scatter, mass, molecular mass, or combinations thereof. In certain embodiments, the detectable label is a fluorophore (i.e., a fluorescent label, fluorescent dye, etc.). Fluorophores of interest may include, but are not limited to, dyes suitable for use in analytical applications (e.g., flow cytometry, imaging, etc.).

In some instances, the fluorophore (i.e., dye) is a polymeric dye (e.g., a fluorescent polymeric dye). Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. The structural characteristics of the polymeric dyes can have an effect on the fluorescence properties of the molecules.

Any convenient polymeric dye may be utilized in the subject devices and methods. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer), and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via Forster energy transfer.

Polymeric dyes of interest include, but are not limited to, those dyes described by Gaylord et al. in U.S. Publication Nos. 20040142344, 20080293164, 20080064042, 20100136702, 20110256549, 20120028828, 20120252986 and 20130190193, the disclosures of which are herein incorporated by reference in their entirety; and Gaylord et al., *J. Am. Chem. Soc.*, 2001, 123 (26), pp 6417-6418; Feng et al., *Chem. Soc. Rev.*, 2010,39, 2411-2419; and Traina et al., *J. Am. Chem. Soc.*, 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some cases, the hydrophilic water soluble group is charged, e.g., positively or negatively charged. In certain cases, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula $-(CH_2-CH_2-O-)_n-$, or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky, "Functionalized poly(ethylene glycol) for preparation of biologically relevant conjugates", *Bioconjugate Chemistry* 1995, 6(2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, $-COOM'$, $-SO_3M'$, $-PO_3M'$, $-NR_3^+$, Y', $(CH_2CH_2O)_pR$ and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, $-(CH_2CH_2O)_{yy}CH_2CH_2XR^{yy}$, $-(CH_2CH_2O)_{yy}CH_2CH_2X-$, —X(CH$_2$CH$_2$O)$_{yy}$CH$_2$CH$_2$—, glycol, and polyethylene glycol, wherein yy is selected from 1 to 1000, X is selected from O, S, and NR$^{ZZ}$, and R$^{ZZ}$ and R$^{YY}$ are independently selected from H and C$_{1-3}$ alkyl.

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments.

The polymeric dyes may be of any convenient molecular weight (MW). In some cases, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

In certain instances, the polymeric dye includes the following structure:

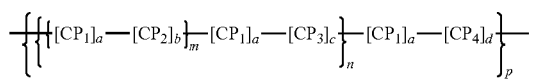

where CP$_1$, CP$_2$, CP$_3$ and CP$_4$ are independently a conjugated polymer segment or an oligomeric structure, wherein one or more of CP$_1$, CP$_2$, CP$_3$ and CP$_4$ are bandgap-lowering π-conjugated repeat units, and each n and each m are independently 0 or an integer from 1 to 10,000 and p is an integer from 1 to 100,000.

In some instances, the polymeric dye includes the following structure:

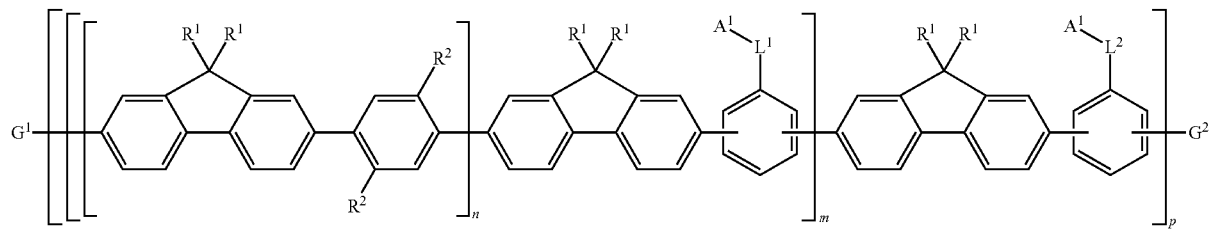

where each R$^1$ is independently a solubilizing group or a linker-dye; L$^1$ and L$^2$ are optional linkers; each R$^2$ is independently H or an aryl substituent; each A$^1$ and A$^2$ is independently H, an aryl substituent or a fluorophore; G$^1$ and G$^2$ are each independently selected from the group consisting of a terminal group, a π-conjugated segment, a linker and a linked specific binding member; each n and each m are independently 0 or an integer from 1 to 10,000; and p is an integer from 1 to 100,000. Solubilizing groups of interest include alkyl, aryl and heterocycle groups further substituted with a hydrophilic group such as a polyethylglycol (e.g., a PEG of 2-20 units), an ammonium, a sulphonium, a phosphonium, and the like.

In some cases, the polymeric dye includes, as part of the polymeric backbone, a conjugated segment having one of the following structures:

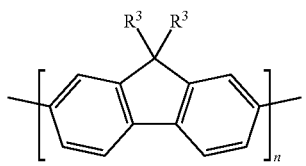

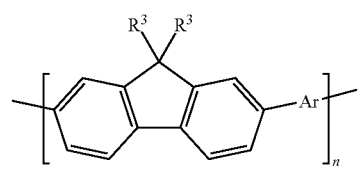

where each R$^3$ is independently an optionally substituted alkyl or aryl group; Ar is an optionally substituted aryl or heteroaryl group; and each n is an integer from 1 to 10,000. In certain embodiments, R$^3$ is an optionally substituted alkyl group. In certain embodiments, R$^3$ is an optionally substituted aryl group. In some cases, R$^3$ is substituted with a polyethyleneglycol, a dye, a chemoselective functional group or a specific binding moiety. In some cases, Ar is substituted with a polyethyleneglycol, a dye, a chemoselective functional group or a specific binding moiety.

In some instances, the polymeric dye includes the following structure:

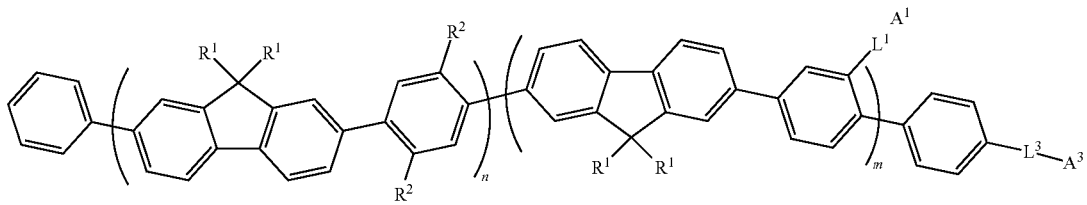

where each $R^1$ is independently a solubilizing group or a linker-dye group; each $R^2$ is independently H or an aryl substituent; each $L^1$ and $L^3$ are independently optional linkers; each $A^1$ and $A^3$ are independently H, a fluorophore, a functional group or a specific binding moiety (e.g., an antibody); and n and m are each independently 0 or an integer from 1 to 10,000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." *Cytometry Part A,* 81A (6), 456-466, 2012).

In some embodiments, the polymeric dye has an absorption curve between 280 nm and 475 nm. In certain embodiments, the polymeric dye has an absorption maximum (excitation maximum) in the range 280 nm and 475 nm. In some embodiments, the polymeric dye absorbs incident light having a wavelength in the range between 280 nm and 475 nm.

In some embodiments, the polymeric dye has an emission maximum wavelength ranging from 400 nm to 850 nm, such as 415 nm to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410 nm to 430 nm, 500 nm to 520 nm, 560 nm to 580 nm, 590 nm to 610 nm, 640 nm to 660 nm, 700 nm to 720 nm, and 775 nm to 795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

In some instances, the polymeric dye has an extinction coefficient of $1\times10^6$ cm$^{-1}$M$^{-1}$ or more, such as $2\times10^6$ cm$^{-1}$M$^{-1}$ or more, $2.5\times10^6$ cm$^{-1}$M$^{-1}$ or more, $3\times10^6$ cm$^{-1}$M$^{-1}$ or more, $4\times10^6$ cm$^{-1}$M$^{-1}$ or more, $5\times10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, or even more. In certain cases, the polymeric dye has a quantum yield of 0.1 or more. In certain cases, the polymeric dye has a quantum yield of 0.3 or more. In certain cases, the polymeric dye has a quantum yield of 0.5 or more. In some embodiments, the polymeric dye has an extinction coefficient of $1\times10^6$ or more and a quantum yield of 0.3 or more. In some embodiments, the polymeric dye has an extinction coefficient of $2\times10^6$ or more and a quantum yield of 0.5 or more.

In certain embodiments, as described above, the reagent device includes more than one dye composition, such as, for example, two dye compositions (e.g., first and second dye compositions). In these embodiments, the dye compositions can be polymeric dye compositions, as described above. For example, the reagent device may include first and second polymeric dye compositions. As described above, the first and second polymeric dyes may be conjugated polymers (CPs). In certain cases, the first and second polymeric dyes are water soluble conjugated polymers, as described above. In some instance, the dye compositions included in the reagent device may be different dye compositions, such as different polymeric dye compositions. Different dye compositions may differ from each other in terms of chemical composition and/or in terms of one or more properties of the dyes. For instance, different dye compositions may differ from each other by at least one of excitation maxima and emission maxima. In some cases, different dye compositions differ from each other by their excitation maxima. In some cases, different dye compositions differ from each other by their emission maxima. In some cases, different dye compositions differ from each other by both their excitation maxima and emission maxima. As such, in embodiments that include first and second dyes, the first and second dyes may differ from each other by at least one of excitation maxima and emission maxima. For example, the first and second dyes may differ from each other by excitation maxima, by emission maxima, or by both excitation and emission maxima. Additional dye compositions may be included in the reagent device, where each of the dye compositions in the reagent device differ from each other as described above.

In certain embodiments, the reagent device also includes other types of dye compositions, such as one or more non-polymeric dye compositions. As discussed above, dyes may include detectable moieties or markers that are detectible based on, for example, fluorescence emission maxima, fluorescence polarization, fluorescence lifetime, light scatter, mass, molecular mass, or combinations thereof. In certain embodiments, the non-polymeric dye includes a fluorophore (i.e., a fluorescent label, fluorescent dye, etc.). Fluorophores of interest may include but are not limited to dyes suitable for use in analytical applications (e.g., flow cytometry, imaging, etc.). A large number of non-polymeric dyes are commercially available from a variety of sources, such as, for example, Molecular Probes (Eugene, Oreg.) and Exciton (Dayton, Ohio). For example, the fluorophore of the non-polymeric dye may be 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI);

5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin (PE); o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; carotenoid-protein complexes, such as peridinin-chlorophyll proteins (PerCP); allophycocyanin (APC); or combinations thereof.

In certain embodiments, the dye compositions included in the reagent device include polymeric dye compositions, as described above. In some cases, the dye compositions included in the reagent device include non-polymeric dye compositions, as described above. In some instances, the dye compositions included in the reagent device include both polymeric dye compositions and non-polymeric dye compositions. As described above, each of the dye compositions (e.g., polymeric and non-polymeric dye compositions) may be distinctly positioned on a surface of the solid support of the reagent device. In some cases, the reagent device includes a plurality of dye compositions as described above. For example, the reagent device may include two or more, such as three or more, distinct polymeric dye compositions and two or more, such as three or more, or four or more, or five or more, distinct non-polymeric dye compositions. In some cases, the reagent device includes three or more distinct polymeric dye compositions and five or more distinct non-polymeric dye compositions.

As described above, the reagent device may include both a polymeric dye composition and a non-polymeric dye composition. In some instances, a polymeric dye composition is mixed with a non-polymeric dye composition. In certain embodiments, the mixture of the polymeric dye composition and the non-polymeric dye composition do not undergo significant dye-dye interactions between the polymeric dye composition and the non-polymeric dye composition. For instance, the fluorescence emission energy of the polymeric dye composition is not significantly quenched by interactions with the non-polymeric dye composition. In some cases, the fluorescence emission energy of the polymeric dye composition is not significantly dissipated by a non-radiative transition. In these embodiments, the detectable fluorescence of the polymeric dye composition is not significantly less than would be expected as compared to the fluorescence of the polymeric dye composition in the absence of the non-polymeric dye composition. Similarly, in some embodiments, the fluorescence emission energy of the non-polymeric dye composition is not significantly quenched by interactions with the polymeric dye composition. For instance, the fluorescence emission energy of the non-polymeric dye composition may not be significantly dissipated by a non-radiative transition. In these embodiments, the detectable fluorescence of the non-polymeric dye composition is not significantly less than would be expected as compared to the fluorescence of the non-polymeric dye composition in the absence of the polymeric dye composition.

In certain embodiments, the dye composition includes a dye, such as a polymeric and/or non-polymeric dye, as described above. The dye composition may also include other components, such as, but not limited to a solvent, a buffer, a stabilizer, and the like. For example, the dye composition may include a stabilizer that reduces and/or substantially prevents degradation of the dye in the dye composition. In some cases, the presence of a stabilizer in the dye composition is sufficient to reduce and/or substantially prevent degradation of the dye in the dye composition for a certain period of time, such as 24 hours or more, or 48 hours or more, or 72 hours or more, or 4 days or more, or 5 days or more, or 6 days or more, or 1 week or more, or 2 weeks or more, or 3 weeks or more, or 4 weeks or more, or 2 months or more, or 3 months or more, or 4 months or more, or 5 months or more, or 6 months or more, or 9 months or more, or 1 year or more. Examples of stabilizers include, but are not limited to, bovine serum albumin (BSA), sodium azide, glycerol, phenylmethanesulfonyl fluoride (PMSF), and the like. Additional additives may also be present in the composition, such as, additives that preserve cells present in whole blood, e.g., platelet stabilizing factor, and the like. Examples of additives that may be included in the composition are anticoagulants such as ethylenediaminetetraacetic acid (EDTA), buffered citrate, heparin, and the like. The composition may include these additives in a liquid or dried state.

In certain embodiments, the reagent device also includes a calibration standard. The calibration standard may be useful for determining the accuracy of the assay and for ensuring consistency between subsequent assays. In some cases, the calibration standard includes a labelled bead, such as a fluorescently labelled bead. The fluorescently labelled bead may be a standard fluorescently labeled bead that is typically used as a calibration standard. Examples of standard fluorescently labeled beads include, but are not limited to, fluorescently labelled microparticles or nanoparticles. In some cases, the fluorescently labeled beads are configured such that they remain suspended in the assay mixture and do not substantially settle or aggregate. In some embodiments, the fluorescently labeled beads include, but are not limited to, fluorescently labelled polystyrene beads, fluorescein beads, rhodamine beads, and other beads tagged with a fluorescent dye. Additional examples of fluorescently labeled beads are described in U.S. Pat. Nos. 6,350,619; 7,738,094; and 8,248,597, the disclosures of each of which are herein incorporated by reference in their entirety.

In some cases, the reagent devices facilitate storage of the dye composition for an extended period of time. For instance, a reagent device may be a storage stable reagent device. In some cases, the dye compositions contained in the reagent device are storage stable dye compositions, where the dye compositions are substantially stable for an extended period of time. By "stable" or "storage stable" or "substantially stable" is meant a dye composition that does not significantly degrade and/or lose activity over an extended period of time. For example, a storage stable dye composition may not have significant loss of fluorescence activity due to degradation of the dye composition over an extended period of time, such as 10% or less loss of fluorescence activity, or 9% or less, or 8% or less, or 7% or less, or 6% or less, or 5% or less, or 4% or less, or 3% or less, or 2% or less, or 1% or less loss of fluorescence activity over an extended period of time. In certain instances, a storage stable dye composition has 5% or less loss of fluorescence activity over an extended period of time. In some cases, a storage stable dye composition substantially retains its fluorescence activity over an extended period of time, such as retains 100% of its activity, or 99% or more, or 98% or more, or 97% or more, or 96% or more, or 95% or more, or 94% or more, or 93% or more, or 92% or more, or 91% or more, or 90% or more, or 85% or more, or 80% or more, or 75% or more of its activity over an extended period of time. For example, a storage stable dye composition may retain 90% or more of its fluorescence activity over an extended period of time. In some cases, a storage stable composition retains 95% or more of its fluorescence activity over an extended period of time. An extended period of time is a period of time such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. For instance, an extended period of time may be 6 months or more. In some cases, an extended period of time is 9 months or more. In some cases, an extended period of time is 1 year (e.g., 12 months) or more. In some cases, an extended period of time is 1.5 years (e.g., 18 months) or more. In some cases, an extended period of time is 2 years (e.g., 24 months) or more. In some instances, the extended period of time is 10 years or less, such as 7.5 years or less, including 5 years or less, e.g., 2 years or less.

An example of a reagent device according to embodiments of the present disclosure is shown in FIG. 1. In FIG. 1, the reagent device 10 is configured as a vial or test tube; e.g., the reagent device 10 includes a solid support 12 in the form of a vial (test tube). The reagent device 10 includes three different dried polymeric dye compositions (14, 16, 18) on a surface of the solid support 12.

The three polymeric dye compositions (14, 16, 18) on a surface of the solid support 12 are distinctly positioned relative to each other on the surface of the solid support 12.

Methods of Use

Aspects of the present disclosure also include methods of using the subject reagent device. As described above, the reagent device may include a solid support and one or more polymeric dye compositions (e.g., first and second polymeric dye compositions) distinctly positioned on a surface of the solid support. The polymeric dye compositions may be dried polymeric dye compositions. As such, the method of using the reagent device includes reconstituting the dye composition. In certain embodiments, the method includes combining a volume of a liquid and the reagent device in a manner sufficient to produce a reconstituted dye composition. The volume of liquid may be added to the reagent device using any convenient liquid handling apparatus, such as, but not limited to, syringes, needles, pipets, aspirators, among other liquid handling devices.

In some cases, as described above, the solid support is configured as a liquid container, and as such includes an inner surface and an outer surface. As described above, the inner surface of the liquid container one or more dried polymeric dye compositions. In these cases, the combining step of the method may include positioning the volume of liquid inside the liquid container. By positioning the volume of liquid inside the liquid container, the liquid may contact the dried polymeric dye compositions on the inner surface of the liquid container. In some cases, the liquid (e.g., water) may be absorbed by the dried polymeric dye compositions, thus reconstituting the dried polymeric dye compositions.

In certain embodiments, the liquid includes a biological sample. In some cases, the biological sample may be derived from specific biological fluids, such as, but not limited to, blood, mucus, lymphatic fluid, synovial fluid, cerebrospinal fluid, saliva, bronchoalveolar lavage, amniotic fluid, amniotic cord blood, urine, vaginal fluid and semen. In some embodiments, the biological sample includes whole blood or a fraction thereof. In some embodiments, the biological sample includes blood plasma.

In certain embodiments, the reagent device is a sealed reagent device, such as where the reagent device includes a seal (e.g., a water-tight and/or air-tight seal). In these instances, the method may include removing the seal prior to positioning the volume of liquid inside the liquid container. Removing the seal on the reagent device may expose the contents of the liquid container to the surrounding environment and allow access to the interior volume of the liquid container. Thus, a user that has access to the interior volume of the liquid container may positioning the volume of liquid inside the liquid container for reconstitution of the dried polymeric dye compositions inside the liquid container.

In certain embodiments, the method also includes mixing the contents of the liquid container after positioning the volume of liquid inside the liquid container. The mixing may be performed using any convenient protocol. For example, the mixing may be performed using an agitator. The agitator may be any convenient agitator sufficient for mixing the liquid inside the liquid container, including, but not limited to, vortexers, sonicators, shakers (e.g., manual, mechanical, or electrically powered shakers), rockers, oscillating plates, magnetic stirrers, static mixers, rotators, blenders, mixers, tumblers, orbital shakers, among other agitating protocols.

In some cases, the method also includes assaying the reconstituted dye composition. Assaying the reconstituted dye composition may be performed using any suitable assay apparatus. For example, the assay apparatus may be a flow cytometer. In these embodiments, the assaying includes flow cytometrically analyzing the reconstituted dye composition. In some instances, the assaying includes contacting the reconstituted dye composition with electromagnetic radiation (e.g., light), such as electromagnetic radiation having a wavelength that corresponds to the excitation maxima of the reconstituted dye composition. The assaying may further include detecting emitted light from the excited dye compositions. For instance, the method may include detecting emitted light from the excited dye compositions at one or more wavelengths that correspond to the emission maxima of the dye compositions.

Suitable flow cytometry systems and methods for analyzing samples that may be employed in methods of the invention include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACScan™, and BD Biosciences FACSCalibur™ systems, BD Biosciences Influx™ cell sorter, BD Biosciences Accuri™ C6 flow cytometer; BD Biosciences LSRFortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FACSJazz™ flow cytometer, or the like. In certain embodiments, the subject systems are flow cytometric systems, such those described in U.S. Pat. Nos. 3,960,449; 4,347,935; 4,667,830; 5,245,318; 5,464,581; 5,483,469; 5,602,039; 5,643,796; 5,700,692; 6,372,506 and 6,809,804 the disclosure of which are herein incorporated by reference in their entirety.

Other methods of analysis may also be used, such as, but not limited to, liquid chromatography-mass spectrometry or gas chromatography-mass spectrometry systems. For example, assaying may include the use of an analytical separation device such as a liquid chromatograph (LC), including a high performance liquid chromatograph (HPLC), a micro- or nano-liquid chromatograph or an ultra-high pressure liquid chromatograph (UHPLC) device, a capillary electrophoresis (CE), or a capillary electrophoresis chromatograph (CEC) apparatus. Mass spectrometer (MS) systems may also be used to assay the dye compositions. Examples of mass spectrometers may include, but are not limited, to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof.

In certain embodiments, the reagent device is included in an apparatus that is fully automated. By "fully automated" is meant that the apparatus receives a reagent device and prepares a reconstituted dye composition with little to no human intervention or manual input into the subject systems. In certain embodiments, the subject systems are configured to prepare and analyze the reconstituted dye composition without any human intervention.

In certain embodiments, the method also includes storing the reconstituted dye composition for a period of time. The reconstituted dye composition may be stored for a period of time before, during and/or after assaying the reconstituted dye composition. In some instances, the reconstituted dye composition is stored for a period of time such as 24 hours or more, or 48 hours or more, or 72 hours or more, or 4 days or more, or 5 days or more, or 6 days or more, or 1 week or more, or 2 weeks or more, or 3 weeks or more, or 4 weeks or more, or 2 months or more, or 3 months or more, or 4 months or more, or 5 months or more, or 6 months or more, or 9 months or more, or 1 year or more. In certain cases, the reconstituted dye composition is stored for 24 hours or more. In certain cases, the reconstituted dye composition is stored for 48 hours or more. In certain cases, the reconstituted dye composition is stored for 72 hours or more. In certain cases, the reconstituted dye composition is stored for 1 week or more. In certain cases, the reconstituted dye composition is stored for 2 weeks or more. In certain cases, the reconstituted dye composition is stored for 3 weeks or more.

Embodiments of the method may further include shipping the reconstituted dye composition to a remote location. A "remote location," is a location other than the location at which the dye composition is reconstituted. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or one hundred miles or more apart.

Methods of Making

Aspects of the present disclosure also include methods of making a reagent device as described herein. In certain embodiments, the method of making includes distinctly positioning one or more dye compositions on a surface of the solid support. For example, the method of making may include distinctly positioning two or more dye compositions (e.g., first and second dye compositions) on a surface of the solid support. In some instances, the dye compositions are polymeric dye compositions (e.g., first and second polymeric dye compositions) distinctly positioned on a surface of the solid support, as described herein.

As described herein, the polymeric dye compositions may be dried polymeric dye compositions. As such, the method of making may include positioning a dried polymeric dye composition on a surface of the solid support. Dried polymeric dye compositions may be positioned on the surface of the solid support using any convenient protocol, such as, but not limited to, spraying, printing, or other deposition method.

In certain embodiments, the dye composition is positioned on the surface of the solid support first and then the dye composition is dried to provide a dried dye composition on the surface of the solid support. In these embodiments, the dye composition may be provided as a liquid dye composition and the liquid dye composition may be distinctly positioned on the surface of the solid support. The distinctly positioned liquid dye composition may be dried to provide a distinctly positioned dried dye composition on the surface of the solid support. The liquid dye composition may be distinctly positioned on the surface of the solid support using any convenient liquid handling apparatus, such as, but not limited to, syringes, needles, pipets, aspirators, among other liquid handling devices. In some instances, the liquid dye composition may be distinctly positioned on the surface of the solid support using a printer, such as, but not limited to, an inkjet printer. A liquid dye composition that is distinctly positioned on the surface of the solid support may be dried using any convenient drying protocol. In some cases, the solid support may be heated or placed in an environment at a temperature greater than standard conditions. In certain instances, the temperature is a temperature greater than standard conditions that is sufficient to dry the liquid dye composition, but less than a temperature that would cause degradation to the dye composition. For example, the solid support may be heated to a temperature ranging from 30° C. to 50° C., such as 30° C. to 45° C. to provide a dried dye composition. In certain embodiments, the temperature is applied to the solid support for a time sufficient to dry the dye composition, such as 1 min or more, or 5 min or more, or 10 min or more, or 15 min or more, or 20 min or more, or 30 min or more. In embodiments that include two or more dye compositions on the surface of the solid support, the different dye compositions may be positioned and dried on the surface of the solid support sequentially, or each dye composition may be positioned on the surface of the solid support and all of the dye compositions may be dried simultaneously.

As described herein, the reagent device may include two or more dye compositions (e.g., polymeric dye compositions) distinctly positioned on a surface of a solid support. As such, in some cases, the method includes positioning the dye compositions at separate locations on the surface of the solid support. For example, the method may include positioning first and second polymeric dye compositions at separate locations on the surface of the solid support. Additional dye compositions may be provided on the surface of the solid support, such as a third polymeric dye composition. In these embodiments, the method may further include distinctly positioning the third polymeric dye composition on the surface of the solid support. Additional polymeric and/or non-polymeric dye compositions may also be distinctly positioned on the surface of the solid support.

In certain embodiments, the reagent device includes two or more dye compositions (e.g., polymeric dye compositions) co-located at the same location of the surface of the solid support. Accordingly, in these embodiments the method may include co-locating the dye compositions at the same location of the surface of the solid support. For example, the method may include co-locating first and second dye compositions (e.g., first and second polymeric dye compositions) at the same location of the surface of the solid support. In some cases, the method also includes positioning a non-dye material between the co-located dye compositions. For instance, the method may include positioning a non-dye material between the first and second polymeric dye compositions. Additional dye compositions may be co-located at the same location of the surface of the solid support, such as a third polymeric dye composition. In these embodiments, the method may further include distinctly positioning the third polymeric dye composition at the same location of the surface of the solid support. Additional polymeric and/or non-polymeric dye compositions may also be distinctly positioned at the same location of the surface of the solid support.

After positioning the dye compositions on the surface of the solid support (e.g., liquid container), the method may further include sealing the solid support (e.g., liquid container). For example, the method may include applying a seal to the liquid container. As described above, the seal may be a water-tight and/or an air-tight seal. In some instances, the seal is a removable or a breakable seal, which allows a user to subsequently gain access to the contents of the liquid container.

As described above, the reagent device may also include a calibration standard, such as standard fluorescently labelled beads. In these embodiments, the method may further include positioning a set of standard fluorescently labelled beads on the surface of the solid support. The positioning may be performed using any convenient technique for handling beads. For example, the beads may be provided in a liquid, such as a suspension of beads in a liquid. In these instances, the liquid containing the beads may be positioned on the surface of the solid support using any convenient liquid handling apparatus, such as, but not limited to, syringes, needles, pipets, aspirators, among other liquid handling devices. In some instances, the liquid containing the beads may be positioned on the surface of the solid support using a printer, such as, but not limited to, an inkjet printer.

Kits

Aspects of the disclosure also include kits that include a subject reagent device. In certain embodiments, the kit includes a subject reagent device and a packaging configured to hold the reagent device. The packaging may be a sealed packaging, e.g., a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). The kits may further include a buffer. For instance, the kit may include a buffer, such as a sample buffer, a wash buffer, an assay buffer, and the like. The kits may further include additional reagents, such as but not limited to, detectable labels (e.g., fluorescent labels, colorimetric labels, chemiluminescent labels, multicolor reagents, avidin-streptavidin associated detection reagents, radiolabels, gold particles, magnetic labels, etc.), and the like. In certain embodiments, the kits may also include a calibration standard. For example, the kits may include a set of labelled beads, such as a set of standard fluorescently labelled beads.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

Utility

The subject reagent devices and methods find use in applications where cell analysis from a biological sample may be desired for research, laboratory testing or for use in therapy. In some embodiments, the subject reagent devices and methods facilitate analysis of cells obtained from fluidic or tissue samples such as specimens for diseases, including but not limited to cancer. Reagent devices and methods of the present disclosure also allow for analyzing cells from a biological sample (e.g., organ, tissue, tissue fragment, fluid) with enhanced efficiency and low cost.

The subject reagent devices and methods find use in applications where the analysis of a sample using two or more dye compositions is desired. For example, the subject reagent devices and methods find use in applications where the analysis of a sample using two or more polymeric dye compositions is desired. Embodiments of the subject reagent devices and methods also find use in applications where analysis of a sample using two or more polymeric dye compositions in combination with one or more non-polymeric dye compositions is desired. Thus, the subject reagent devices and methods find use in applications where a sample is analyzed for two or more analytes of interest using two or more corresponding polymeric dye compositions. In some cases, where non-polymeric dye compositions are also included in the reagent devices, the subject reagent devices and methods find use in applications where a sample is analyzed for two or more analytes of interest using two or more corresponding polymeric dye compositions and non-polymeric dye compositions.

The subject reagent devices and methods find use in applications where a minimization in dye-dye interactions is desired. As described herein, the subject reagent devices and methods provide two or more dried polymeric dye compositions that are distinctly positioned on a surface of a solid support. As such, the distinct positioning of the dye compositions relative to each other on the surface of the solid support facilitates a minimization in dye-dye interactions. A minimization in dye-dye interactions may facilitate the collection of more precise and/or accurate data with respect to the assays performed using the subject reagent devices. For instance, the subject reagent devices and methods may facilitate a reduction in dye-dye interactions as compared to reagent devices in which two or more dye compositions are provided but are not distinctly positioned relative to each other.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Experiments were performed to produce and test a reagent device having three distinctly positioned dried polymeric dye compositions according to embodiments of the present disclosure.

Figure 2:
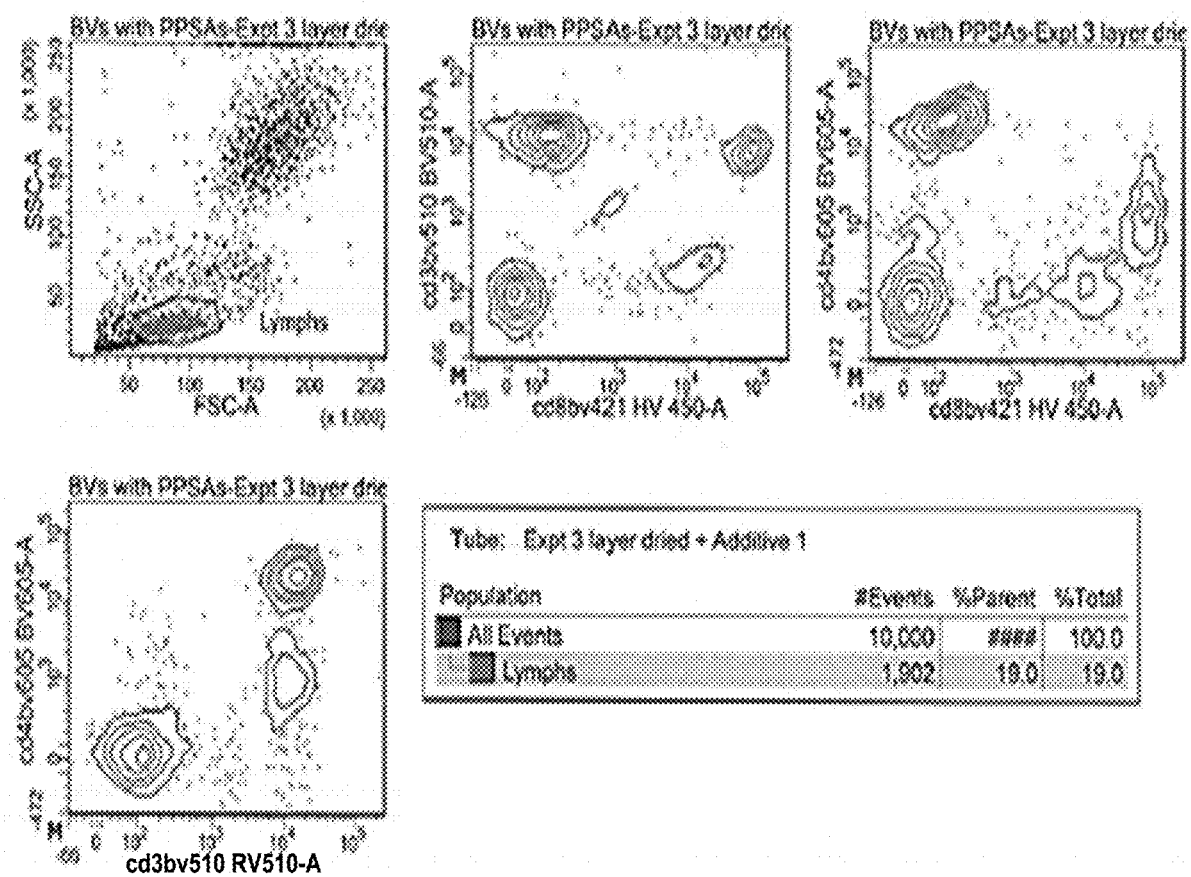
FIG. 2 shows graphs of flow cytometry results from an analysis performed using a reagent device with three distinctly positioned dried polymeric dye compositions, according to embodiments of the present disclosure.

A first polymeric dye composition (BV510, a polymeric dye composition having an excitation maximum at 405 nm and an emission maximum at 510 nm; BD Biosciences, New Jersey) was positioned at a first location on an inner surface of a vial and dried. A second polymeric dye composition (BV421, a polymeric dye composition having an excitation maximum at 407 nm and an emission maximum at 421 nm; BD Biosciences, New Jersey) was distinctly positioned at a second separate location on the inner surface of the vial and dried. A third polymeric dye composition (BV605, a polymeric dye composition that includes a tandem fluorochrome that is a combination of BV421 and Cy™ 3.5 having an excitation maximum at 407 nm and an emission maximum at 602 nm; BD Biosciences, New Jersey) was distinctly positioned at a third separate location on the inner surface of the vial and dried. Cy™ 3.5 is a cyanine dye that can be excited by green (532 nm) and yellow-green (561 nm) lasers. A sample was added to the vial to produce a reconstituted dye composition and analyzed by flow cytometry. Graphs of the assay results are shown in FIG. 2 and indicated that there was a minimization in dye-dye interactions.

Example 2

Experiments were performed to produce and test a reagent device having three distinctly positioned dried polymeric dye compositions and seven non-polymeric dye compositions according to embodiments of the present disclosure.

Figure 3:
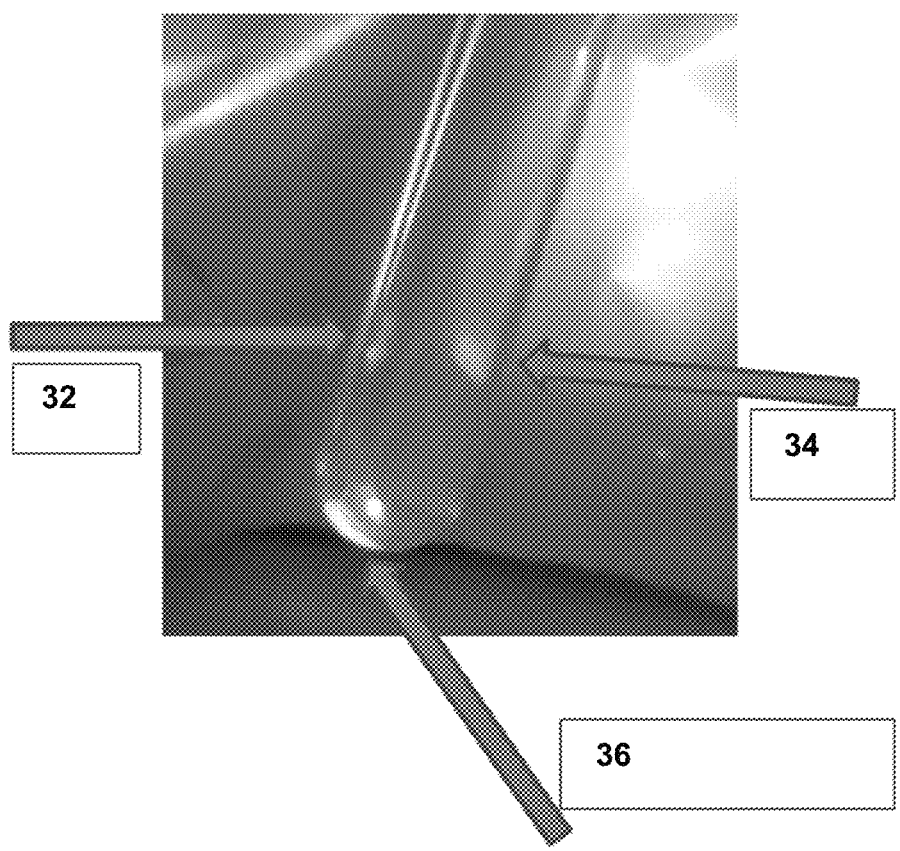
FIG. 3 shows an image of a reagent device that includes three distinctly positioned dried polymeric dye compositions and seven non-polymeric dyes, according to embodiments of the present disclosure.
Figure 4:
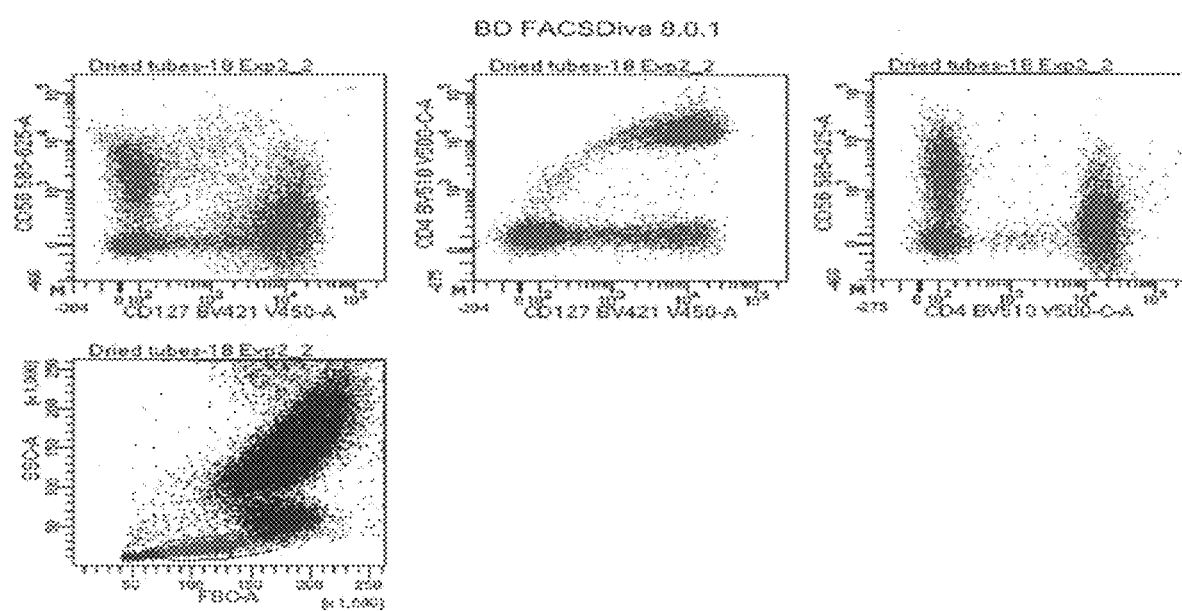
FIG. 4 shows graphs of flow cytometry results from an analysis performed using a reagent device with three distinctly positioned dried polymeric dye compositions and seven non-polymeric dyes, according to embodiments of the present disclosure.

A first polymeric dye composition (BV605, a polymeric dye composition that includes a tandem fluorochrome that is a combination of BV421 and Cy™ 3.5 having an excitation maximum at 407 nm and an emission maximum at 602 nm; BD Biosciences, New Jersey) and a second polymeric dye composition (BV421, a polymeric dye composition having an excitation maximum at 407 nm and an emission maximum at 421 nm; BD Biosciences, New Jersey) were distinctly positioned at a two separate locations on an inner surface of a vial and dried. A third polymeric dye composition (BV510, a polymeric dye composition having an excitation maximum at 405 nm and an emission maximum at 510 nm; BD Biosciences, New Jersey) was distinctly positioned at a third location on an inner surface of a vial and dried. The third polymeric dye composition also included seven different non-polymeric dyes: FITC, PE, PerCP-Cy5.5 conjugate dye, PE-Cy7 conjugate dye, APC, APC-R700 tandem conjugate dye, and APC-H7 (an APC-cyanine tandem dye). An image of the dried polymeric dye compositions on an inner surface of the vial is shown in FIG. 3. As shown in FIG. 3, the first polymeric dye composition 32, the second polymeric dye composition 34, and third polymeric dye composition 36 that also included seven non-polymeric dyes were distinctly positioned on the inner surface of the vial. A sample was added to the vial to produce a reconstituted dye composition and analyzed by flow cytometry. Graphs of the assay results are shown in FIG. 4 and indicated that there was a minimization in dye-dye interactions.

Embodiments

In one embodiment, the present disclosure provides a multiplex polymeric dye device having a solid support, and first and second dried polymeric dye compositions distinctly positioned relative to a surface of the solid support.

In some embodiments, the first and second dried polymeric dye compositions include first and second polymeric dyes that differ from each by at least one of excitation and emission maxima. For example, the first and second polymeric dyes can be water soluble conjugated polymers.

In some embodiments, each of the first and second dried polymeric dye compositions includes a stabilizer.

In some embodiments, the first and second dried polymeric dye compositions are positioned at separate locations on the surface of the solid support. In some embodiments, the distance between the separate locations ranges from 0.1 mm to 200 mm.

In some embodiments, the first and second dried polymeric dye compositions are co-located at the same location of the surface of the solid support. In certain cases, the first and second dried polymeric dye compositions are separated from each other by a non-dye material.

In some embodiments, the device includes a third dried polymeric dye composition distinctly positioned relative to the surface of the solid support.

In some embodiments, the device includes a dried non-polymeric dye composition.

In some embodiments, the device includes three or more distinct dried polymeric dye compositions and five or more distinct dried non-polymeric dye compositions.

In some embodiments, the surface of the solid support includes an inner surface of a liquid container In some embodiments, the liquid container is configured to hold a volume ranging from 0.1 ml to 250 ml. In some embodiments, the liquid container is a vial. In other embodiments, the liquid container is a well of a multi-well plate. In some embodiments, the liquid container is sealed. In some embodiments, the solid support is a glass. In other cases, the solid support is a plastic.

In some embodiments, the device further includes a set of standard fluorescently labelled beads.

In another embodiment, the present disclosure provides a method that includes combining a volume of a liquid and a reagent device in a manner sufficient to produce a reconstituted dye composition. In some embodiments, the reagent device includes a solid support, and first and second dried polymeric dye compositions distinctly positioned relative to a surface of the solid support;

In some embodiments, the liquid includes a biological sample. In some embodiments, the biological sample includes whole blood or a fraction thereof.

In some embodiments, the surface of the solid support is an inner surface of a liquid container and, in these cases, the method includes combining includes positioning the volume of liquid inside of the liquid container.

In some embodiments, the liquid container is sealed and, in these cases, the method includes removing the seal prior to positioning the volume of liquid inside of the liquid container.

In some embodiments, the method further includes assaying the reconstituted dye composition. In some embodiments, the assaying includes flow cytometrically analyzing the reconstituted dye composition.

In some embodiments, the method further includes storing the reconstituted dye composition for a period of time.

In some embodiments, the method further includes shipping the reconstituted dye composition to a remote location.

In another embodiment, the present disclosure provides a method of making a reagent device, where the method includes distinctly positioning first and second dried polymeric dye compositions relative to a surface of a solid support.

In some embodiments, the method further includes sealing the liquid container.

In another embodiment, the present disclosure provides a kit that includes a reagent device, and a packaging configured to hold the reagent device. In some embodiments, the reagent device includes a solid support, and first and second dried polymeric dye compositions distinctly positioned relative to a surface of the solid support.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of embodiments of the present disclosure and are included within its spirit and scope. Furthermore, all examples and conditional language recited herein are principally intended to aid the reader in understanding the principles of embodiments of the present disclosure being without limitation to such specifically recited examples and conditions. Moreover, all statements herein reciting principles, aspects, and embodiments of embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the embodiments of the present disclosure, therefore, is not intended to be limited to the exemplary embodiments shown and described herein. Rather, the scope and spirit of embodiments of the present disclosure are embodied by the appended claims.

What is claimed is:

1. A method of producing a reconstituted dye composition of first and second distinct conjugated polymeric dyes, the method comprising:
   introducing a volume of an aqueous liquid into a container having an inner surface, wherein the container comprises:
   a first dried composition comprising the first conjugated polymeric dye which is dried and adhered onto a first location of the inner surface; and
   a second dried composition comprising the second conjugated polymeric dye which is dried and adhered onto a second location of the inner surface that is separate from the first location so as to minimize dye-dye interaction of the distinct first and second conjugated polymeric dyes;
   to produce the reconstituted dye composition, wherein the first and second polymeric dyes of the reconstituted dye composition exhibit minimal dye-dye interaction.

2. The method according to claim 1, wherein the aqueous liquid comprises a biological sample.

3. The method according to claim 2, wherein the biological sample comprises whole blood or a fraction thereof.

4. The method according to claim 1, wherein the first and second locations are separated by a distance ranging from 0.1 mm to 200 mm.

5. The method according to claim 1, wherein the container comprises a third dried composition comprising a third conjugated polymeric dye which dried and adhered onto a third location of the inner surface that is separate from the first and second locations.

6. The method according to claim 5, wherein the third dried composition further comprises a non-polymeric dye.

7. The method according to claim 1, wherein the container is configured to hold a volume ranging from 0.1 ml to 250 ml.

8. The method according to claim 1, wherein the container is a vial.

9. The method according to claim 1, wherein the container is a well of a multi-well plate.

10. The method according to claim 1, wherein the container is sealed and the method comprises removing the seal prior to positioning the volume of liquid inside of the liquid container.

11. The method according to claim 1, wherein the method further comprises assaying the reconstituted dye composition.

12. The method according to claim 1, wherein the conjugated polymers are water soluble polymers.

13. The method according to claim 1, wherein:
the first dried composition is produced by positioning a liquid composition of the first conjugated polymeric dye at the first location and then drying the positioned liquid composition of the first conjugated polymeric dye at the first location to produce the first dried composition; and
the second dried composition is produced by positioning a liquid composition of the second conjugated polymeric dye at the second location and then drying the positioned liquid composition of the second conjugated polymeric dye at the second location to produce the second dried composition.

* * * * *